(12) United States Patent
Choi et al.

(10) Patent No.: US 10,478,636 B2
(45) Date of Patent: Nov. 19, 2019

(54) LIGHT THERAPY DEVICE FOR RHINITIS OR TYMPANITIS TREATMENT

(71) Applicant: EVORAY CO. LTD., Chungcheongbuk-do (KR)

(72) Inventors: Jeongho Choi, Chungcheongbuk-do (KR); Bokhyeon Jeon, Chungcheongbuk-do (KR)

(73) Assignee: EVORAY CO. LTD., Cheongju-si, Chungcheongbuk-do (KR)

( * ) Notice: Subject to any disclaimer, the term of this patent is extended or adjusted under 35 U.S.C. 154(b) by 131 days.

(21) Appl. No.: 14/787,271

(22) PCT Filed: May 13, 2014

(86) PCT No.: PCT/KR2014/004258
§ 371 (c)(1),
(2) Date: Oct. 27, 2015

(87) PCT Pub. No.: WO2015/174556
PCT Pub. Date: Nov. 19, 2015

(65) Prior Publication Data
US 2016/0166847 A1    Jun. 16, 2016

(51) Int. Cl.
*A61N 5/06* (2006.01)

(52) U.S. Cl.
CPC ...... *A61N 5/0603* (2013.01); *A61N 2005/063* (2013.01); *A61N 2005/0605* (2013.01); *A61N 2005/0607* (2013.01); *A61N 2005/0647* (2013.01); *A61N 2005/0659* (2013.01)

(58) Field of Classification Search
CPC .......... A61N 5/0603; A61N 2005/0605; A61N 2005/0607; A61N 2005/063; A61N 2005/0647; A61N 2005/0659; A61N 5/06
USPC ...................................... 607/88–94
See application file for complete search history.

(56) References Cited

U.S. PATENT DOCUMENTS

| | | | | |
|---|---|---|---|---|
| 5,683,436 A | * | 11/1997 | Mendes | A61N 5/0603 607/88 |
| 6,358,272 B1 | * | 3/2002 | Wilden | A61N 5/0603 606/13 |

FOREIGN PATENT DOCUMENTS

KR   10-2012-0039407    4/2012

\* cited by examiner

*Primary Examiner* — Lynsey C Eiseman
(74) *Attorney, Agent, or Firm* — Revolution IP, PLLC

(57) ABSTRACT

A light therapy device, including: a housing including a hanging part lying over a user's nose and a bridge part connected to the hanging part; a light source positioned inside the housing and emitting light for treatment; and a rhinitis treatment optical guide having a protruding shape inside the housing to be inserted into the user's nose and guiding the light emitted from the light source to the outside.

4 Claims, 8 Drawing Sheets

LIGHT THERAPY DEVICE FOR RHINITIS OR TYMPANITIS TREATMENT

CROSS REFERENCE TO PRIOR APPLICATIONS

This application is a National Stage Application of PCT International Patent Application No. PCT/KR2014/004258 filed on May 13, 2014, under 35 U.S.C. § 371, which is hereby incorporated by reference in its entirety.

BACKGROUND OF THE INVENTION

1. Technical Field

The present invention relates to a light therapy device for rhinitis or tympanitis treatment, and more particularly, to a light therapy device for rhinitis or tympanitis treatment using light such as near infrared rays.

2. Description of the Related Art

Rhinitis generally happens due to an inflammation occurring in the nasal mucous membrane in a nose and is classified into acute rhinitis, chronic rhinitis, and viral rhinitis happening due to the cold. When a patient is infected with rhinitis, he/she may not breathe well and therefore go through symptoms such as headache and attention deficit, such that he/she may suffer from great inconvenience.

To treat the rhinitis, a method of injecting steam of an appropriate temperature into a nose or a method for injecting treatment drug, etc., into a nose has been mainly used. In addition, a technology of treating an inflammation in a nose using infrared rays has been known.

The infrared rays have been proven to be effective in treating rhinitis and tympanitis and therefore have been widely used in an otolaryngology, etc. By the way, Korean Patent Laid-Open Publication No. 10-2012-0039407 (Portable apparatus for curing rhinitis published on Apr. 25, 2012) discloses a portable apparatus for curing rhinitis. However, to actually use the apparatus for curing rhinitis, a user needs to hold the portable apparatus for curing rhinitis against a nose while holding it in his hand. For this reason, the user may have considerable limitations in other works or activities during the treatment.

SUMMARY OF THE INVENTION

An object of the present invention is to provide a light therapy device for rhinitis or tympanitis treatment which enables a user to freely use his/her both hands while a user treats rhinitis or tympanitis.

According to an exemplary embodiment of the present invention, there is provided a light therapy device, including: a housing including a hanging part lying over a user's nose and a bridge part connected to the hanging part; a light source positioned inside the housing and emitting light for treatment; and a rhinitis treatment optical guide having a protruding shape inside the housing to be inserted into the user's nose and guiding the light emitted from the light source to the outside.

The light source may be positioned inside the housing and the rhinitis treatment optical guide may have a shape protruding from one side of the housing. The light therapy device may further include: a tympanitis terminal having a tympanitis treatment light source emitting the light for treatment provided therein and having a shape inserted into a user's ear, wherein the tympanitis terminal is detachably coupled with the housing to be electrically connected to the housing. The tympanitis terminal may include the tympanitis treatment optical guide guiding the light emitted from the tympanitis treatment light source to the outside provided at an end thereof. The tympanitis treatment optical guide may be detachably coupled with the tympanitis terminal. The light therapy device may further include: a battery positioned inside the housing and supplying power to the light source.

The housing may include: a hanging part lying over the user's nose; a pair of accommodating parts connected to both sides of the hanging part, respectively and accommodating the light source; and a pair of bridge parts connected to the pair of accommodating parts, respectively and provided to lie over a user's ear. The bridge may be made of a flexible material or an elastic material.

The rhinitis treatment optical guide may be made of a flexible material and may be detachably coupled with the housing.

DESCRIPTION OF THE EXEMPLARY EMBODIMENTS

Exemplary embodiments of the present invention will be described in more detail with reference to the accompanying drawings.

Figure 1:
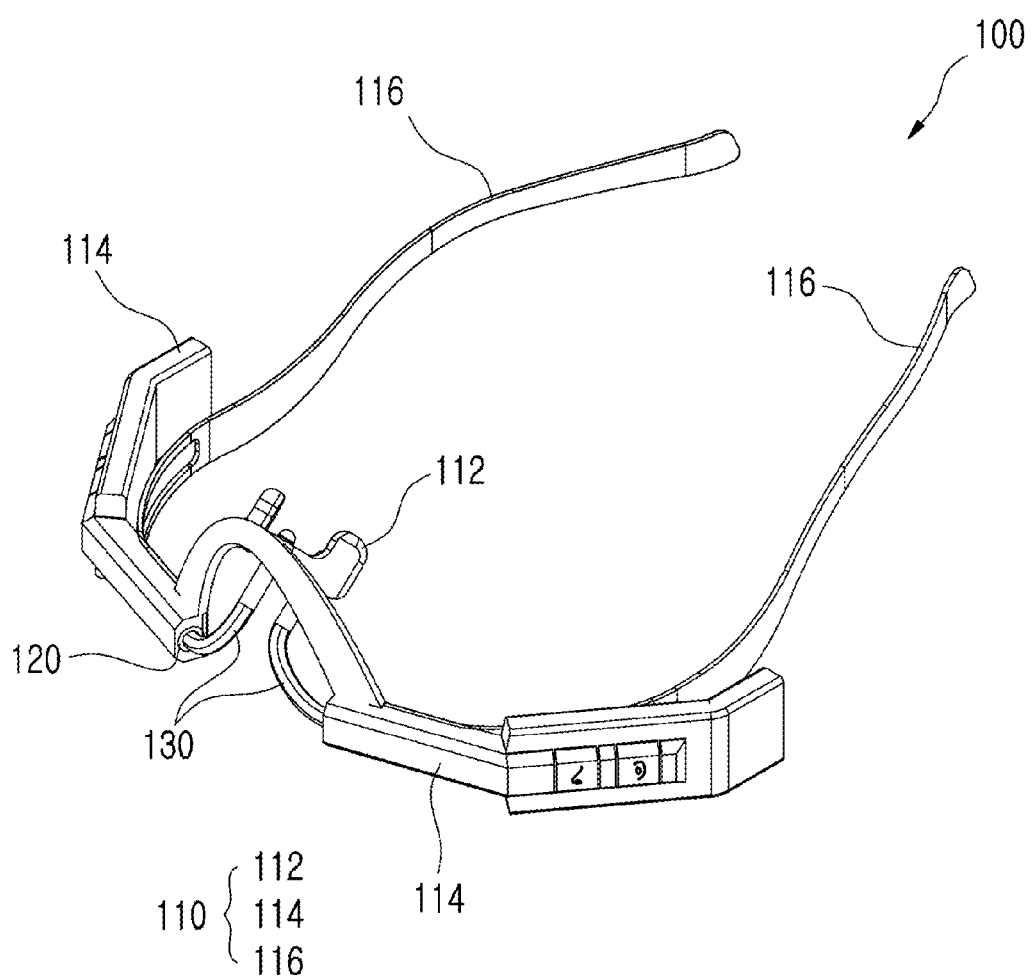
FIG. 1 is a diagram illustrating a light therapy device according to an exemplary embodiment of the present invention.

As illustrated in FIG. 1, a light therapy device 100 according to an exemplary embodiment of the present invention is configured to include a housing 110, a rhinitis treatment light source 120, a rhinitis treatment optical guide 130, a tympanitis terminal 140, a control substrate 150, and a battery 160 and will be described with reference to the drawings illustrated in FIGS. 1 to 5.

The housing 110 accommodates the rhinitis treatment light source 120, the rhinitis treatment optical guide 130, the control substrate 150, and the battery 160 and is configured to include accommodating parts 114 and bridge parts 116.

Figure 4:
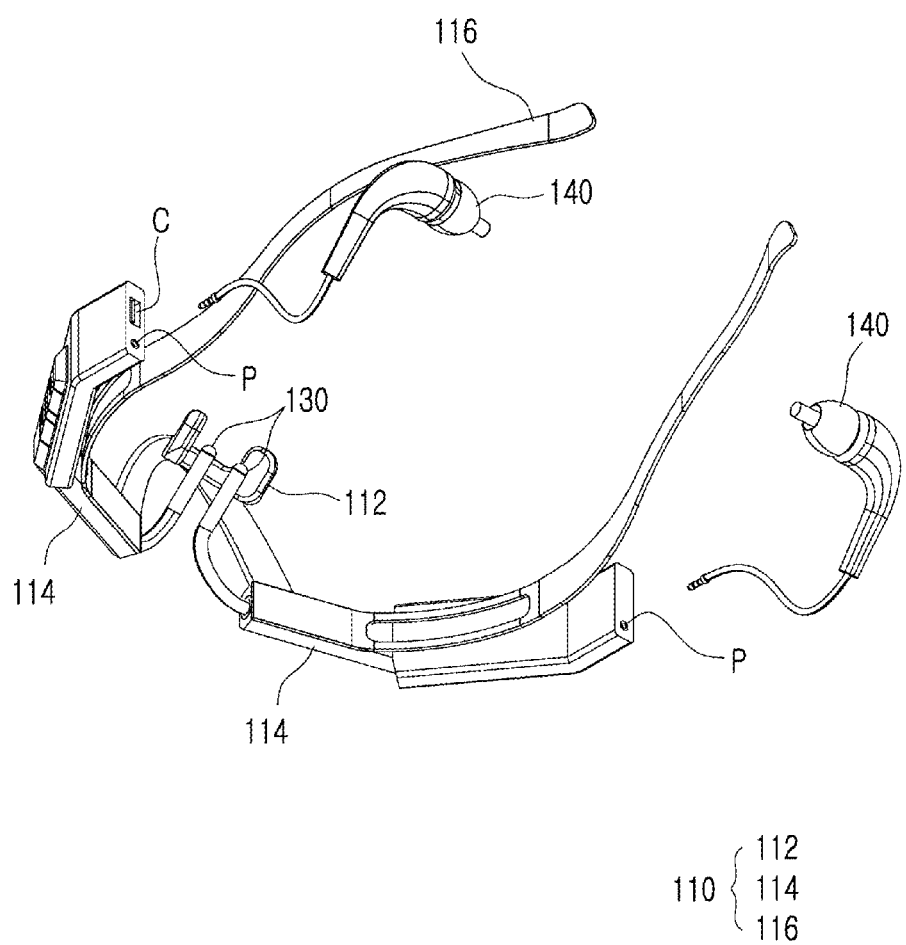
FIG. 4 is a diagram illustrating the light therapy device according to an exemplary embodiment of the present invention viewed from another angle.

As illustrated in FIGS. 1 and 4, the hanging part 112 has a shape concavely warped in one direction to lie over a user's nose while enclosing a user's bridge of nose and may have a shape of a bar or a shape of a plate.

The accommodating part 114 is provided in pair and each of the accommodating parts 114 is connected to both left and right side ends of the hanging part 112. Further, an inside of the accommodating part 114 is provided with an accommodating space in which the rhinitis treatment light source 120, the control substrate 150, and the battery 160 are accommodated and the accommodating part 114 may be preferably made of a synthetic material such as plastic.

Referring to the shape of the accommodating part 114 illustrated in FIG. 1, the accommodating part 114 extends as much as a predetermined length from the hanging part 112 in one direction, is bent, and again extends as much as a predetermined length. That is, a middle portion of the accommodating part 114 has a bent shape. That is, the pair of accommodating parts 114 connected to both side ends of the hanging part 112 based on the hanging part 112 has a bent shape depending on a user's face shape.

Figure 3:
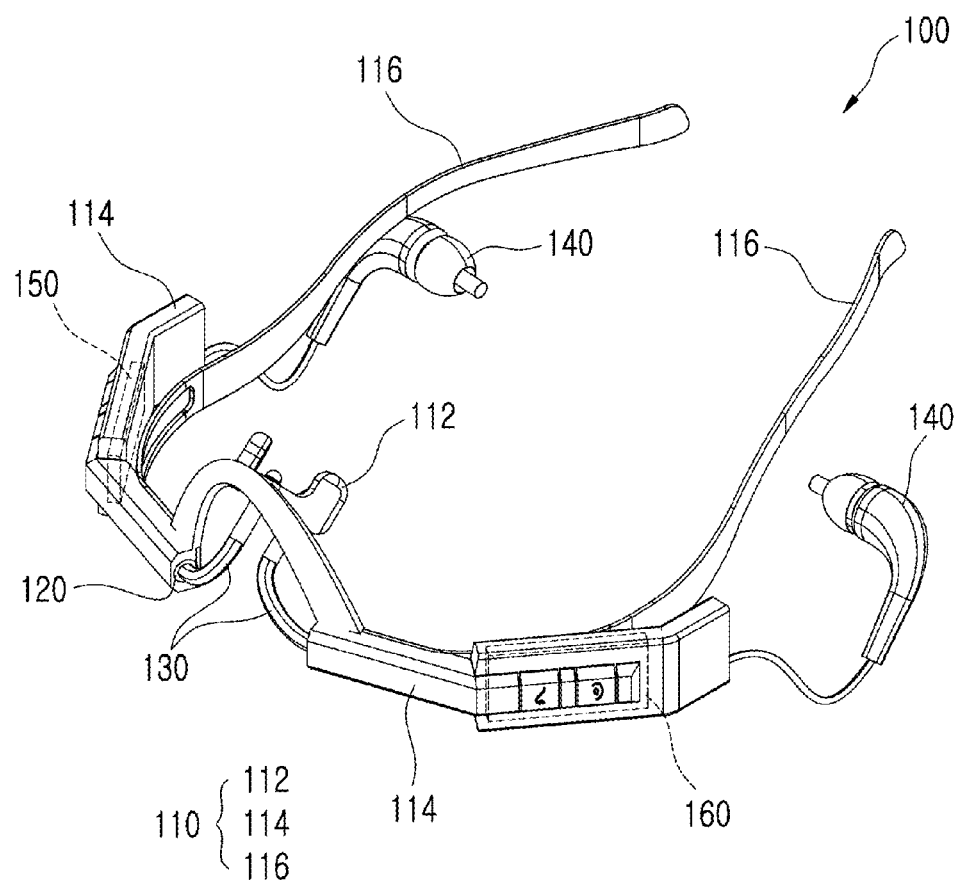
FIG. 3 is a diagram illustrating internal components of the light therapy device according to an exemplary embodiment of the present invention.

As illustrated in FIG. 3, the exemplary embodiment of the present invention will be described the case in which each of the pair of accommodating parts 114 accommodates one rhinitis treatment light source 120, the left accommodating part 114 accommodates the battery 160, and the right accommodating part 114 accommodates the control substrate 150.

In this case, the rhinitis treatment light source 120 is preferably accommodated inside one side end of the accommodating part 114 so that the position where the rhinitis treatment light source 120 is accommodated becomes a predetermined distance from the hanging part 112. Further, the battery 160 and the control substrate 150 each are preferably accommodated inside the other side end of the accommodating part 114 so that they becomes a predetermined distance from the hanging part 112. Therefore, when a user puts on the light therapy device 100 according to the exemplary embodiment of the present invention, the rhinitis treatment light source 120 is positioned at both sides of the hanging part 112 so that it is positioned in front of the face and the battery 160 and the control substrate 150 are positioned both left and right sides of the face.

Figure 2:
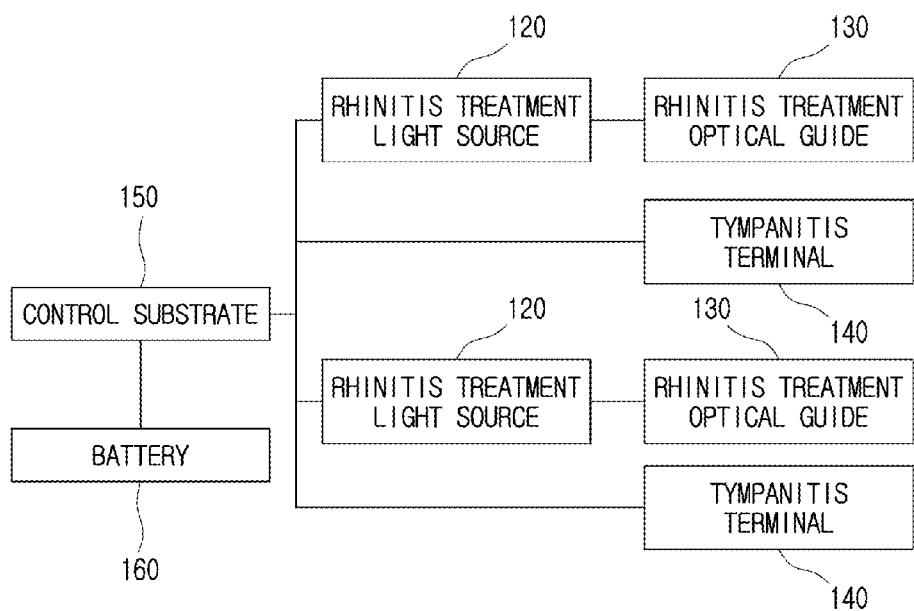
FIG. 2 is a block diagram illustrating a configuration of the light therapy device according to an exemplary embodiment of the present invention to emit light.

Further, as illustrated in FIG. 2, the pair of rhinitis treatment light sources 120, the control substrate 150, and the battery 160 need to be connected to one another, and therefore are connected to one another by an electric wire, etc. For this purpose, although not illustrated, the electric wire may penetrate through the inside of the hanging part 112 connected to the pair of accommodating parts 114.

Further, bridge parts 116 extend from the other sides of the pair of accommodating parts 114, respectively. The bridge part 116 extends from the accommodating part 114 to lie over the user's ear, such that the light therapy device 100 may be put on the user's face.

The pair of bridge parts 116 is made of a flexible material or an elastic material and thus the shape thereof may be deformed by the user if necessary or the pair of bridge parts 116 may be preferably manufactured to adhere to the user's face.

As described above, the rhinitis treatment light source 120 is provided in two and is accommodated in the pair of accommodating parts 114, respectively. Further, light approaching the infrared rays is emitted to power supplied from the battery 160 through the control substrate 150 and according to the exemplary embodiment of the present invention, light having a wavelength of about 660 nm is emitted.

The rhinitis treatment optical guide 130 protrudes from one side of the accommodating part 114 to the outside and as illustrated in FIG. 1, protrudes while having a bar shape. Further, the rhinitis treatment optical guide 130 guides the light emitted from the rhinitis treatment light source 120 to be emitted to the outside. That is, the light emitted from the rhinitis treatment light source 120 is emitted to the outside through the rhinitis treatment optical guide 130 and therefore as the rhinitis treatment optical guide 130, an optical fiber, etc., is used.

One side end of the accommodating part 114 is provided with a hole into which the rhinitis treatment optical guide 130 may be inserted and the rhinitis treatment light source 120 is positioned inside the hole. Therefore, the rhinitis treatment optical guide 130 is inserted into the hole of the accommodating part 114 to connect the rhinitis treatment optical guide 130 to the rhinitis treatment light source 120, such that the light emitted from the rhinitis treatment light source 120 may be emitted to the outside through the rhinitis treatment optical guide 130. That is, the rhinitis treatment optical guides 130 may be detachably coupled with each other in the accommodating part 114.

The rhinitis treatment optical guide 130 may be freely bent or warped in a bar shape. Therefore, the rhinitis treatment optical guide 130 is formed to be inserted into the user's nose in a protruding form in the accommodating part 114.

Figure 5:
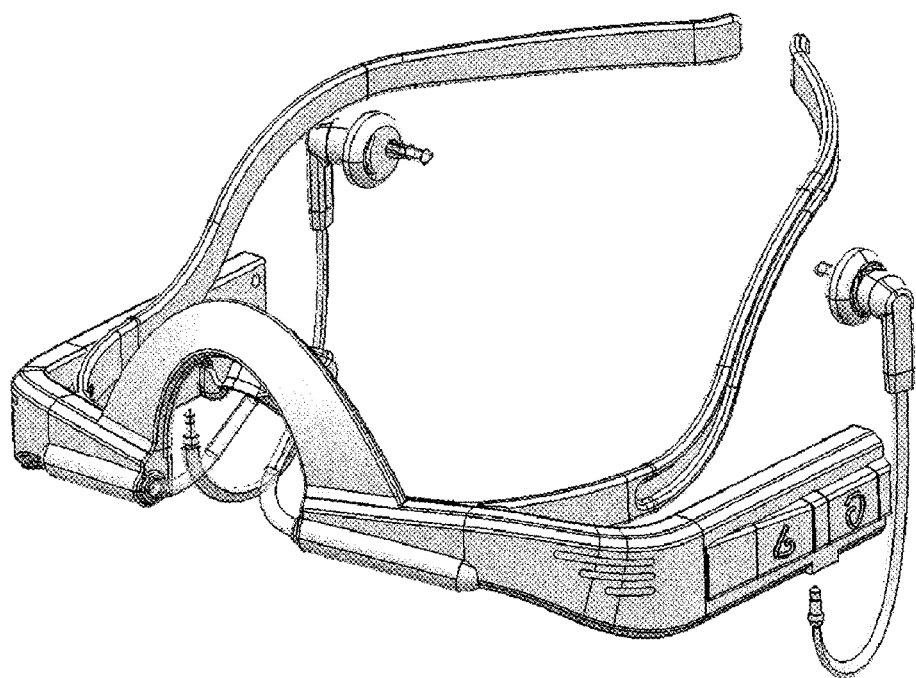
FIGS. 5 and 6 are an actual design for commercialization of the light therapy device according to the exemplary embodiment of the present invention.

That is, as illustrated in FIG. 5, when the user puts the light therapy device 100 on his/her face, the pair of rhinitis treatment optical guides 130 is each inserted into the user's nose and the hanging part 112 lies over the user's bridge of nose to prevent the rhinitis treatment optical guide 130 from falling into the user's nose. Further, the accommodating parts 114 are disposed at both sides of the user's face, such that the light therapy device 100 may be fixed to the user's face.

Further, the rhinitis treatment optical guide 130 may be detached from the accommodating part 114 and therefore the user uses the light therapy device 100 according to the exemplary embodiment of the present invention and then separates the rhinitis treatment optical guide 130 and easily washes the rhinitis treatment optical guide 130.

The tympanitis terminal 140 is to emit light for treating tympanitis into the user's ear and one side of the tympanitis terminal 140 is detachably connected to the housing 110 and the other side thereof has a shape which may be inserted into the user's ear, that is, a similar shape to a typical earphone. Similar to the rhinitis treatment optical guide 130, the tympanitis terminal 140 may be detachably coupled with a tympanitis treatment optical guide 144 consisting of the optical fiber, etc.

Further, referring to FIG. 4, the accommodating part 114 is provided with an insertion port P through which the tympanitis terminal 140 ma be detached. The insertion port P is electrically connected to the control substrate 150 of the accommodating part 114 to supply power to the tympanitis terminal 140. Further, an inside of the tympanitis terminal 140 accommodates a separate tympanitis treatment light source 142 from the rhinitis treatment optical guide 130. The tympanitis treatment light source 142 may emit the light for treatment by the power received from the control substrate 150 side through the insertion port P.

Further, when the tympanitis terminal 140 does not accommodate a separate light source, the optical fiber is mounted in the accommodating part 114 of the insertion port P to be connected to the rhinitis treatment light source 120, such that the light emitted from the rhinitis treatment light source 120 may be emitted through the tympanitis terminal 140 when the tympanitis terminal 140 is connected to the insertion port P.

The control substrate 150 is mounted to receive power from the battery 160, supply power to the rhinitis treatment light source 120, and control the rhinitis treatment light source 120. Further, the control substrate 150 is provided with a plurality of switches which may be exposed to the outside. In this case, the switch may be a power supply switch of the rhinitis treatment light source 120, a use switching switch to the tympanitis terminal 140, etc.

The battery 160 supplies power to the rhinitis treatment light source 120 and the control substrate 150. Further, a charging port C which may charge the battery 160 from the outside is mounted in the accommodating part 114.

Figure 6:
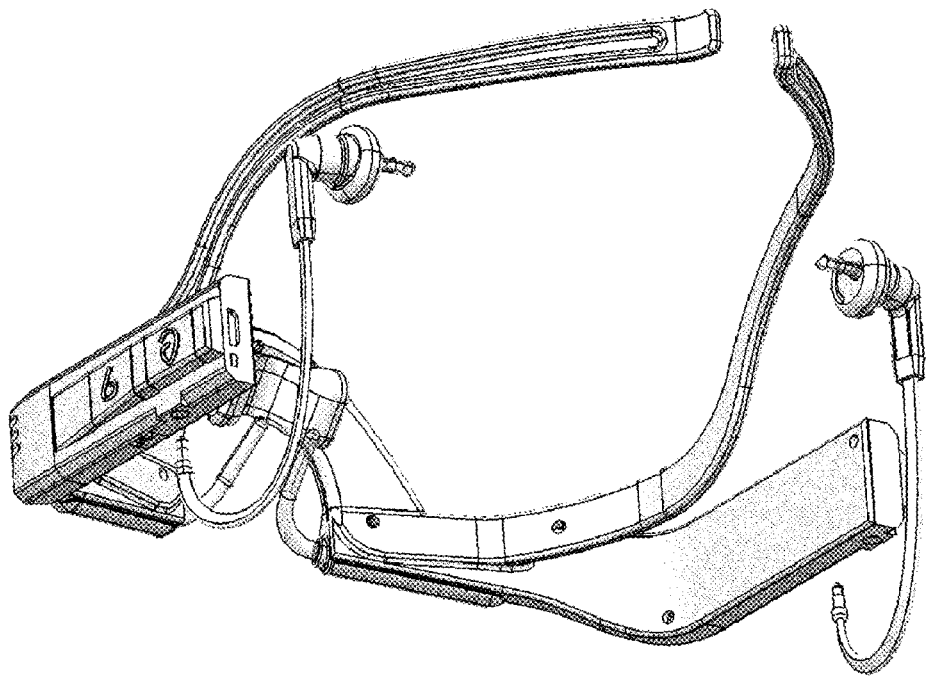
Figure 7:
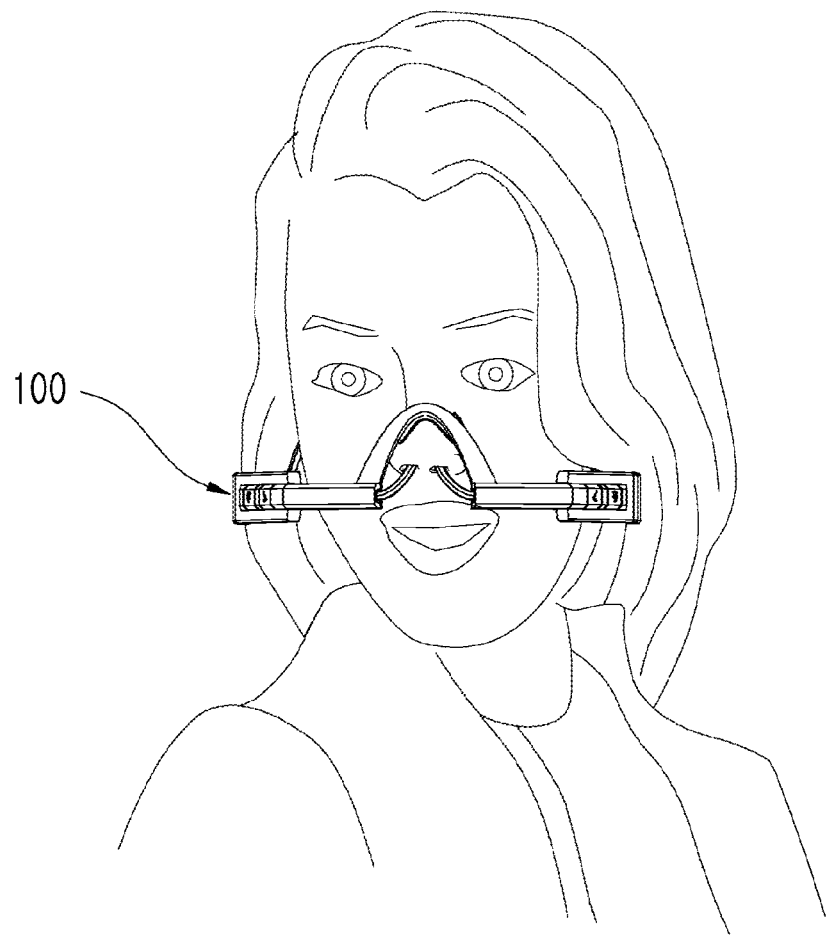
FIG. 7 is a diagram illustrating a state in which a user puts on the light therapy device according to the exemplary embodiment of the present invention.

FIGS. 5 and 6 are an actual design for commercialization of the light therapy device according to the exemplary embodiment of the present invention. This is to increase the flexibility of the shape and the design completion and there is only the difference in a form and a position depending thereon. Therefore, functions and configurations are not changed.

Figure 8:
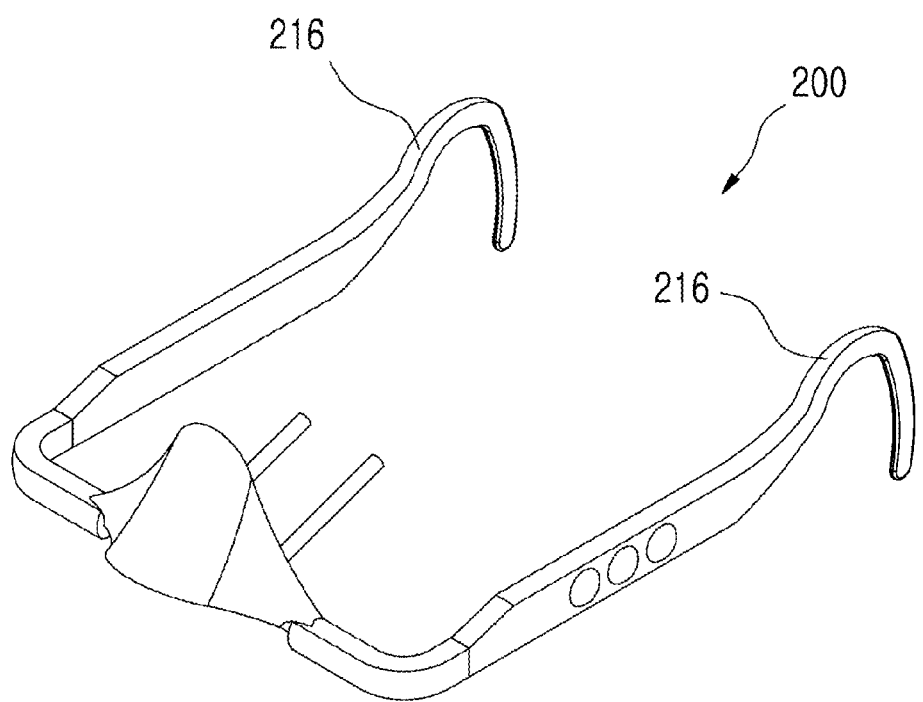
FIG. 8 is a diagram illustrating a light therapy device according to another exemplary embodiment of the present invention.

Meanwhile, FIG. 8 illustrates a light therapy device 200 according to another exemplary embodiment of the present invention, in which an accommodating part 214 and a bridge part 216 may be integrally formed. Other configurations in addition to the shape in which the accommodating part 214 and the bridge part 216 are integrally formed are the same as those of the exemplary embodiment of the present invention and therefore the description thereof will be omitted.

In the light therapy device 200 according to another exemplary embodiment of the present invention, the shape of the bridge part 216 may have a shape enclosing the user's ear like a glasses leg. Therefore, when the user puts on the light therapy device 200, the light therapy device 200 may be stably put on.

According to the exemplary embodiments of the present invention, the user may put on the light therapy device as if he/she puts on glasses, and therefore the user's both hands are free while he/she treats the rhinitis or the tympanitis using light, such that the user may perform other works or activities.

In addition, if children have a short auditory canal and nasal cavity and thus are infected with the rhinitis due to the cold, they may frequently be infected with the tympanitis. The light therapy device according to the exemplary embodiment of the present invention may simultaneously treat the rhinitis and the tympanitis.

Further, the tympanitis terminal for treating tympanitis may be detached from the light therapy device, and therefore may be freely used by the user if necessary.

Although the detailed description of the present invention as described above is made with reference to the accompanying drawings, the foregoing exemplary embodiments are just described with reference to the preferred example of the present invention and therefore the present invention is not understood as being limited only to the exemplary embodiment and the scope of the present invention is to be understood as the claims and the equivalent concept to be described below.

What is claimed is:

1. A light therapy device, comprising:
a housing including a hanging part configured to lie over a user's nose, a pair of accommodating parts connected to both sides of the hanging part, respectively and accommodating a light source, and a pair of bridge parts connected to the pair of accommodating parts, respectively and provided to lie over a user's ear, each of the accommodating parts including an end thereof, the ends of the accommodating parts being positioned under the hanging parts and being opposite to each other;
wherein the light source comprises a pair of light sources positioned inside the pair of accommodating parts respectively and emitting light for treatment;
a pair of rhinitis treatment optical guides detachably coupled with the ends of the accommodating parts, having a shape protruding from the ends of the accommodating parts so that the rhinitis treatment optical guides continue to be inserted in user's nostrils when the hanging part lies over the user's nose after inserting the rhinitis treatment optical guides into the user's nostrils and guiding the light emitted from the pair of light sources to an outside of the housing;
a battery positioned inside the housing and configured to supply power to the light sources; and
a control substrate positioned inside the housing and configured to include a switch for controlling the power to be supplied to the light sources.

2. The light therapy device of claim 1, further includes:
a pair of tympanitis terminals having a tympanitis treatment light sources emitting light for tympanitis treatment provided therein, detachably coupled with other ends of the accommodating parts to supply power from the battery to the tympanitis treatment light sources and having a shape to be inserted into a user's ear; and
a pair of tympanitis treatment optical guides guiding the light emitted from the tympanitis treatment light sources through ends of the tympanitis terminals,
wherein the battery supplies the power to the tympanitis treatment light source, and the control substrate further includes a use control switch for controlling the power to switch from the pair of light sources to the tympanitis treatment light sources.

3. The light therapy device of claim 2, wherein the tympanitis treatment optical guide is detachably coupled with the tympanitis terminal.

4. The light therapy device of claim 1, wherein the ends of the accommodating parts are configured to be positioned under the user's nose.

* * * * *